United States Patent
Meier et al.

(10) Patent No.: US 8,672,679 B2
(45) Date of Patent: Mar. 18, 2014

(54) DENTAL TOOL

(75) Inventors: Friedrich Wilhelm Meier, Blomberg (DE); Markus Niemeier, Lage (DE)

(73) Assignee: Gebr. Brasseler GmbH & Co. KG (DE)

( * ) Notice: Subject to any disclaimer, the term of this patent is extended or adjusted under 35 U.S.C. 154(b) by 0 days.

(21) Appl. No.: 13/176,234

(22) Filed: Jul. 5, 2011

(65) Prior Publication Data
US 2012/0009543 A1    Jan. 12, 2012

(30) Foreign Application Priority Data
Jul. 7, 2010    (DE) .................... 10 2010 026 334

(51) Int. Cl.
*A61C 3/02*    (2006.01)
(52) U.S. Cl.
USPC ............................................. 433/165
(58) Field of Classification Search
USPC ............ 433/165, 166; 407/53, 55, 58, 59, 61, 407/13, 19, 60, 62, 63; 408/199–203; 606/80
See application file for complete search history.

(56) References Cited

U.S. PATENT DOCUMENTS

| | | | | |
|---|---|---|---|---|
| 3,456,316 A | * | 7/1969 | Dawson | 407/53 |
| 6,234,725 B1 | * | 5/2001 | Campian | 407/54 |
| 2007/0166664 A1 | * | 7/2007 | Meier et al. | 433/165 |

FOREIGN PATENT DOCUMENTS

| | | |
|---|---|---|
| DE | 555440 | 7/1932 |
| DE | 202007018284 | 7/2008 |
| DE | 102007009304 | 8/2008 |
| GB | 753233 | 7/1956 |
| GB | 2405365 | 3/2005 |
| JP | 63047007 | 2/1988 |

OTHER PUBLICATIONS

European Search Report dated Oct. 20, 2011 for counterpart European patent application.

* cited by examiner

*Primary Examiner* — Eric Rosen
(74) *Attorney, Agent, or Firm* — Timothy J. Klima; Shuttleworth & Ingersoll, PLC

(57) ABSTRACT

A dental tool includes a working head 3 rotatable about a rotational axis 1 and attached to a shaft 2, which working head is provided with cutting edges 4, 5. Cutting edges 4 of a first toothing are formed about a complete periphery of the working head 3, cutting edges 5 of a second toothing are formed additionally at sector-type partial regions of the working head 3, and sector-type regions are provided at a front face 6 of the working head 3, in which the cutting edges 4, 5 of the first and second toothing end alternatingly in the circumferential direction.

17 Claims, 5 Drawing Sheets

DENTAL TOOL

Figure 1:
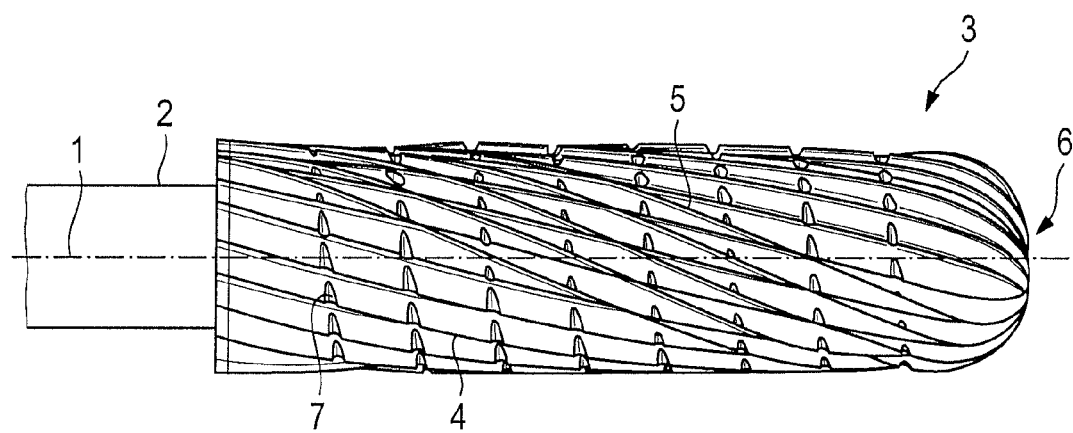

This application claims priority to German Patent Application DE 10 2010 026 334.6-43 filed Jul. 7, 2010, the entirety of which is incorporated by reference herein.

The invention relates to a dental tool.

In detail, the invention refers to a surgical tool or a dental milling cutter including a working head supported on a rotatable shaft, wherein the working head is provided with cutting edges having different toothings.

From the state of the art, dental milling cutters or surgical milling cutters are known, in which a base toothing is provided which is arranged uniformly about the complete periphery of the working head. In addition to this base toothing, a cross toothing can be applied, which is directed into the same or the opposite twisting direction with respect to the base toothing. Also, this cross toothing is distributed uniformly about the complete periphery. In addition, the state of the art also provides embodiments in which a chip breaker groove is provided in a helical manner in a longitudinal direction to the working head, in order to decrease chip length and chip width.

It is an object underlying the invention to provide a dental tool or a surgical tool which shows a good removal performance as well as a high running smoothness while having a simple structure and being manufactured simply and at low costs.

According to the invention, it is thus provided that cutting edges of a first toothing are first formed about the complete periphery of the working head. Said cutting edges preferably extend in parallel to each other and are distributed uniformly about the periphery. In the front-face portion, they still extend substantially in parallel to each other as a kind of group toothing.

According to the invention, it is now provided that cutting edges of a second toothing are formed in addition to the first toothing at sector-type partial regions of the working head, i.e. at partial regions extending only around a part of the periphery.

In a particularly preferable embodiment of the invention, the first toothing and the second toothing are formed either with the same twisting direction or an opposite twisting direction.

According to the invention, it is thus provided that, in individual sectors (with respect to an axially perpendicular sectional plane) about the periphery of the working head, a first toothing and a second toothing are provided, or that only the first toothing is provided in individual sectors.

The inventive dental tool features an enhanced running smoothness and has an increased removal performance, wherein the processed surface has a better surface quality.

At the front face of the working head, the inventive dental tool also comprises sector-type portions in which cutting edges of the first toothing and/or the cutting edges of the second toothing end (alternating in the circumferential direction). Thus, also the front-face end of the inventive dental tool features an enhanced cutting performance.

In a particularly preferable embodiment of the invention, it is provided that the working head has a cylindrical basic shape and/or is rounded at the front face.

In a front view, the sector-type arrangement of the second toothing results in a formation of circular sectors or quadrants at the front face, which are respectively formed by the incoming cutting edges of the first toothing and/or the incoming cutting edges of the second toothing.

Figure 2:
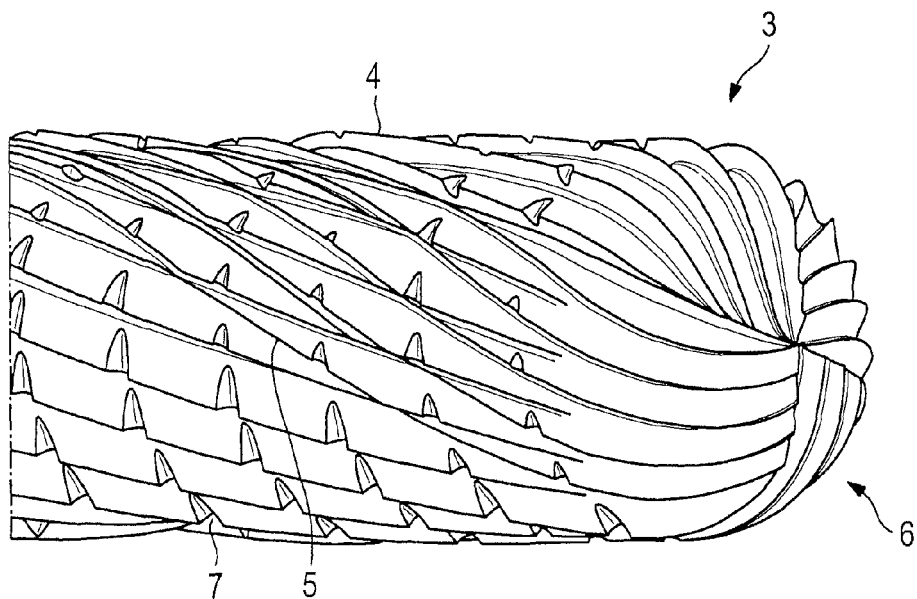
Figure 3:
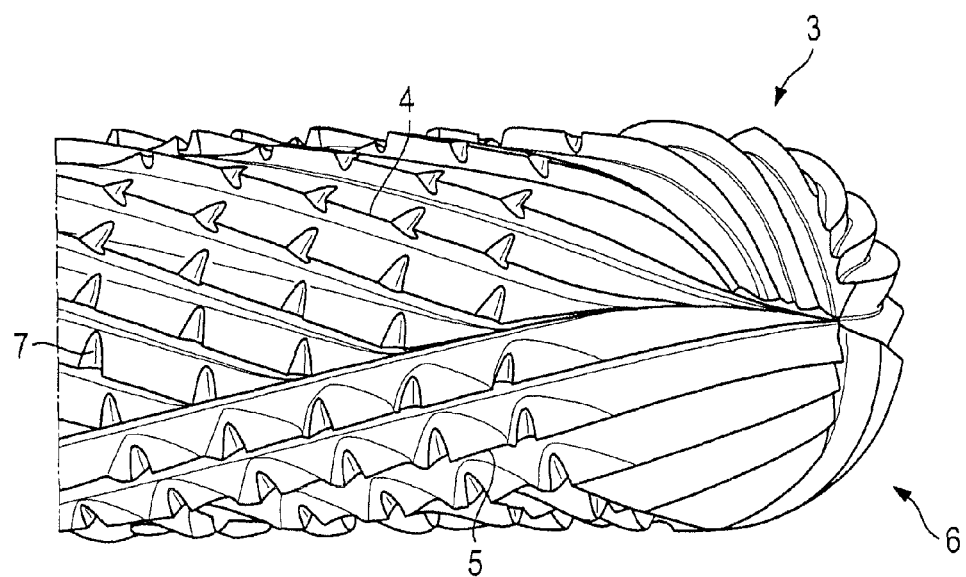
Figure 4:
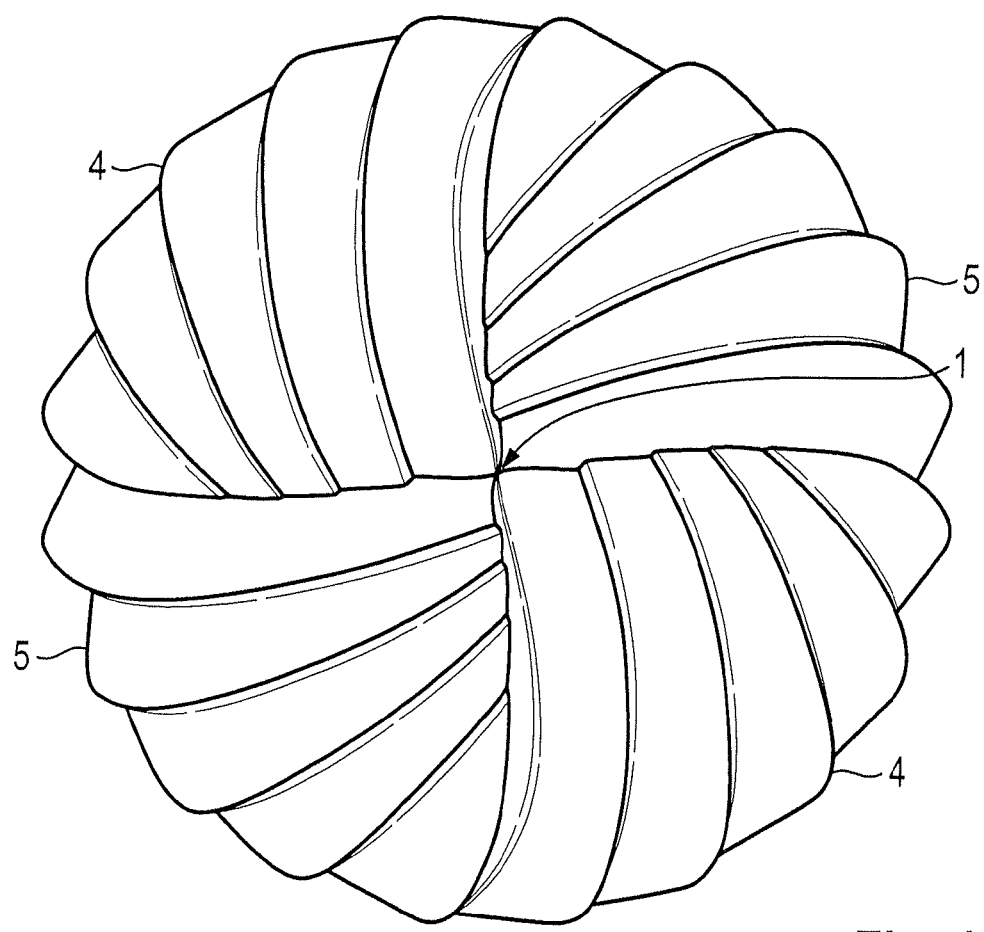
Figure 5:
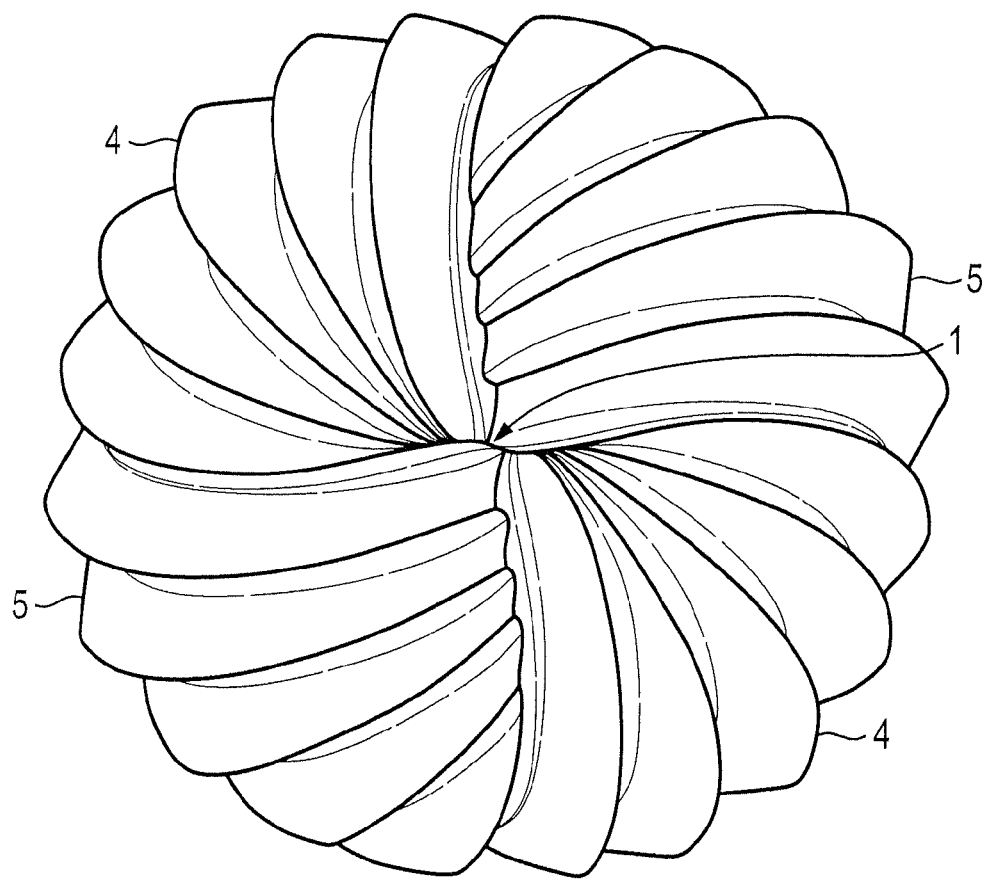
Figure 6:
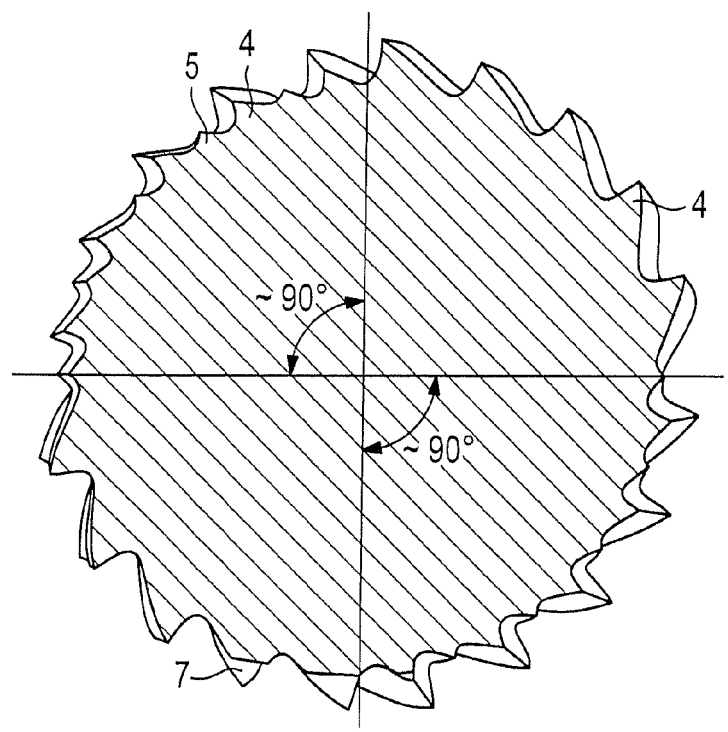
Figure 7:
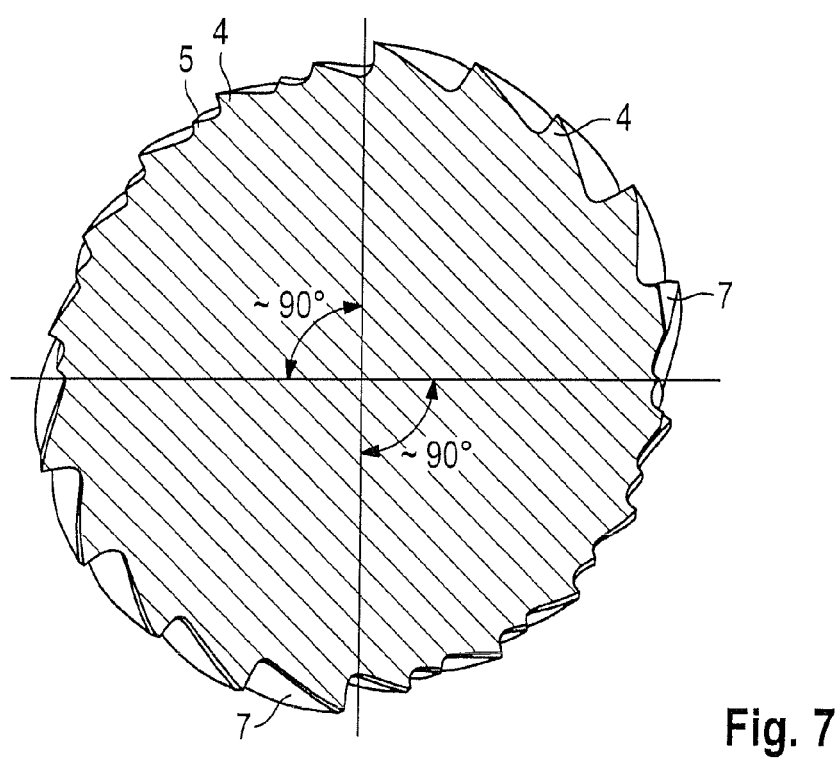

In the following, the invention is described on the basis of embodiments in combination with the drawing, in which:

FIG. 1 shows a side view of a first embodiment of the invention,

FIG. 2 shows a perspective view of the end portion of the embodiment shown in FIG. 1, FIG. 3 shows a perspective view, analogue to FIG. 2, of an opposite twisting direction of the first and second toothings, FIG. 4 shows a front-face view of the embodiments of FIGS. 1 and 2, FIG. 5 shows a further front-face view, analogue to FIG. 4, FIG. 6 shows a sectional view of the embodiment of FIG. 3, and FIG. 7 shows a sectional view of the embodiments of FIGS. 1, 2, 4 and 5.

The inventive dental tool has a cylindrical basic shape which is rounded substantially semi-spherically at its front-face end. Said basic shape is initially manufactured mechanically from a suitable material. In a first processing step, first cutting edges 4 of a first toothing are milled by at least one grinding wheel for producing the working head 3. In the shown embodiments, the first toothing 4 is twisted. When viewing the front-side end (see FIGS. 4 and 5), a rotation about a rotational axis 1 occurs in an anti-clockwise direction. The cutting edge geometries are chosen accordingly.

After forming the first toothing 4 by uniformly generating the cutting edges 4 in an orientation parallel to each other and with an equal distance about the complete periphery of the working head 3, a second toothing 5 with cutting edges 5 which also have a right-hand twist is formed in two sectors which respectively have an angular range of approx. 90° (see FIG. 7). Therewith, the embodiment shown in FIGS. 1, 2, 4 and 7 is generated. Also herein, the second toothing 5 is milled by a milling cutter starting from the front-face end portion. The second toothing therewith superimposes partial regions of the first toothing, as it is in particular discernible from FIGS. 1 and 2.

Subsequently, a chip breaker groove 7 is formed, which is arranged helically about the cylindrical portion of the working head 3.

Therewith, it results that only the first toothing 4 or a combination of first toothing 4 and second toothing 5 engages alternating in a circumferential range of approx. 90° about the periphery of the working head 3 upon a rotation about the rotational axis 1.

FIGS. 3 and 6 show a further embodiment in which the first toothing 4 is formed with a right-hand twist and the second toothing 5 is formed with a left-hand twist, as is in particular discernible from FIG. 3. Further, FIG. 3 shows that four quadrants result upon viewing the front face 6 also in this embodiment, said quadrants comprising respectively either only the first toothing 4 or a combination of first toothing 4 and second toothing 5, as is shown in FIG. 6 in a sectional plane perpendicular to the rotational axis 1, analogous to FIG. 7.

It is obvious that the circumferential angular ranges according to FIGS. 6 and 7 of the invention do not have to be equal; rather, it is also possible to provide that the circumferential region covered only by the first toothing 4 is larger or smaller than 90°.

In addition, it is also possible according to the invention to form no group toothing at the front face 6, as e.g. shown in FIGS. 2 to 5, but a centered toothing in which all cutting edges 4 or 5 meet in a center point located on the rotational axis 1. This is only a variation of the front face 6, the remaining toothing (formation of the cutting edges) at the periphery of the cylindrical basic shape is not changed. FIGS. 4 and 5 show that the cutting edges of the first toothing are divided into sectors (4 in the example according to FIGS. 4 and 5) and that the respectively opposite sectors comprise identically outrunning cutting edges, wherein a changeover between parallel and central outrunning cutting edges (sectors top left and bottom right in FIGS. 4 and 5) occurs between the sectors. The second toothing is not provided at the front face in this embodiment and is restricted exclusively to the lateral area.

FIG. 5 shows a view analogous to FIG. 4. The embodiment of FIG. 5 differs from the embodiment of FIG. 4 in that the cutting edges are arranged alternatingly in parallel or running out toward the center. FIG. 5 therewith shows cutting edges running out in parallel in the quadrants top right and bottom left, whereas the cutting edges run out centrally in the other two quadrants (bottom right and top left in FIG. 5).

According to the invention, it is further possible to form the first toothing and the second toothing differently, e.g. with different cutting angles, wedge angles or free angles as well as with different depths of the chip groove.

LIST OF REFERENCE NUMERALS 1 rotational axis
2 shaft
3 working head
4 cutting edge/first toothing
5 cutting edge/second toothing
6 front face
7 chip breaker groove

What is claimed is:

1. A dental tool comprising:
   a shaft rotatable about a rotational axis;
   a working head attached to the shaft and also rotatable about the rotational axis, the working head including:
      a first toothing having a plurality of cutting edges formed around a complete periphery of the working head;
      a second toothing having a plurality of cutting edges formed in addition to the first toothing at sector partial regions of the working head thereby forming first sector regions containing the first toothing and absent the second toothing, and second sector regions containing both the first toothing and the second toothing in an overlapping manner; and
      the cutting edges of at least one chosen from the first and second toothing ending alternatingly in a circumferential direction in sector regions at a front face of the working head;
   wherein the working head is divided into two of the first sector regions and two of the second sector regions with each of the first and second sector regions having an angular range of approximately 90° and with the first sector regions and the second sector regions alternating with one another around a circumference of the working head;
   wherein the first toothing and the second toothing twist around the working head and the first toothing has a different angle of twist than the second toothing.

2. The dental tool of claim 1, wherein at least one chosen from the first and the second toothing is formed in a twisted configuration.

3. The dental tool of claim 2, wherein directions of twist of the twisted configuration are identical.

4. The dental tool of claim 3, wherein at least one chosen from the cutting edges of the first toothing and the cutting edges of the second toothing run out in parallel at the front face.

5. The dental tool of claim 3, wherein the cutting edges of the first toothing and the cutting edges of the second toothing respectively run out toward a center of the front face.

6. The dental tool of claim 3, wherein the cutting edges of the first sector regions run out toward a center of the front face and the cutting edges of adjacent ones of the second sector regions run out in parallel at the front face, and the first and second sector regions alternate in the circumferential direction.

7. The dental tool of claim 2, wherein directions of twist of the twisted configuration are opposing.

8. The dental tool of claim 7, wherein the cutting edges of the first toothing are arranged parallel to each other and the cutting edges of the second toothing are arranged parallel to each other.

9. The dental tool of claim 8, wherein at least one chosen from the cutting edges of the first toothing and the cutting edges of the second toothing run out in parallel at the front face.

10. The dental tool of claim 8, wherein the cutting edges of the first sector regions run out toward a center of the front face and the cutting edges of adjacent second sector regions run out in parallel at the front face, and the first and second sector regions alternate in the circumferential direction.

11. The dental tool of claim 1, wherein the cutting edges of the first toothing and the cutting edges of the second toothing respectively run out toward a center of the front face.

12. The dental tool of claim 1, wherein the working head has a cylindrically shaped body and the front face is convexly rounded extending between the cylindrically shaped body and a center of the front face.

13. The dental tool of claim 1, wherein at least one chosen from the cutting edges of the first toothing and the cutting edges of the second toothing run out in parallel at the front face.

14. The dental tool of claim 1, wherein the cutting edges of the first sector regions run out toward a center of the front face and the cutting edges of adjacent ones of the second sector regions run out in parallel at the front face, and the first and second sector regions alternate in the circumferential direction.

15. The dental tool of claim 1, wherein the second toothing is superimposed over the first toothing in the second sector regions.

16. The dental tool of claim 15, wherein the sector regions at the front face of the working head are extensions of the first and second sector regions and the front face extends from the periphery of the working head to the rotational axis.

17. The dental tool of claim 1, wherein the sector regions at the front face of the working head are extensions of the first and second sector regions and the front face extends from the periphery of the working head to the rotational axis.

* * * * *